(12) United States Patent
Wechter

(10) Patent No.: US 10,376,699 B2
(45) Date of Patent: Aug. 13, 2019

(54) PROGRAMMING TECHNIQUES FOR ELECTRICAL STIMULATION

(71) Applicant: Boston Scientific Neuromodulation Corporation, Valencia, CA (US)

(72) Inventor: David Ernest Wechter, San Francisco, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 148 days.

(21) Appl. No.: 15/354,830

(22) Filed: Nov. 17, 2016

(65) Prior Publication Data

US 2017/0165490 A1    Jun. 15, 2017

Related U.S. Application Data

(60) Provisional application No. 62/267,690, filed on Dec. 15, 2015.

(51) Int. Cl.
*A61N 1/36* (2006.01)
*A61N 1/372* (2006.01)

(52) U.S. Cl.
CPC ..... *A61N 1/36132* (2013.01); *A61N 1/36071* (2013.01); *A61N 1/36189* (2013.01); *A61N 1/37247* (2013.01); *A61N 1/37264* (2013.01)

(58) Field of Classification Search
USPC .................................................. 607/46, 59
See application file for complete search history.

(56) References Cited

U.S. PATENT DOCUMENTS

| | | | |
|---|---|---|---|
| 8,412,345 B2 | 4/2013 | Moffitt | |
| 8,594,797 B2 | 11/2013 | Lee | |
| 8,676,308 B2 | 3/2014 | Moffitt et al. | |
| 2008/0215119 A1* | 9/2008 | Woods | A61N 1/0551 607/59 |
| 2013/0158630 A1 | 6/2013 | Lee | |

(Continued)

FOREIGN PATENT DOCUMENTS

WO    WO-2017105754 A1    6/2017

OTHER PUBLICATIONS

"International Application Serial No. PCT/US2016/062565, International Preliminary Report on Patentability dated Jun. 28, 2018", 8 pgs.

(Continued)

*Primary Examiner* — Nicole F Lavert
(74) *Attorney, Agent, or Firm* — Schwegman Lundberg & Woessner, P.A.

(57) ABSTRACT

An example includes machine-implemented method of providing therapy to a patient using a plurality of electrodes implanted within the patient that includes receiving, via a programmer for an electrical stimulator, user input that at least partially defines a neuromodulation field to provide the therapy, based on the received user input, determining a subset of the plurality of electrodes and current distributions for the subset to generate the field, comparing an electrode limit to a number of electrodes in the determined subset and eliminating at least one of the number of electrodes in the determined subset based on the comparison to provide a reduced subset of the electrodes, and redistributing current associated with the at least one eliminated electrode to at least one of the electrodes in the reduced subset of electrodes.

20 Claims, 10 Drawing Sheets

(56) References Cited

U.S. PATENT DOCUMENTS

2015/0134031 A1  5/2015  Moffitt et al.
2015/0217116 A1  8/2015  Parramon et al.

OTHER PUBLICATIONS

"International Application Serial No. PCT/US2016/062565, International Search Report dated Mar. 1, 2017", 5 pgs.
"International Application Serial No. PCT/US2016/062565, Written Opinion dated Mar. 1, 2017", 6 pgs.

* cited by examiner

PROGRAMMING TECHNIQUES FOR ELECTRICAL STIMULATION

CLAIM OF PRIORITY

This application claims the benefit of priority under 35 U.S.C. § 119(e) of U.S. Provisional Patent Application Ser. No. 62/267,690, filed on Dec. 15, 2015, which is herein incorporated by reference in its entirety.

TECHNICAL FIELD

This document relates generally to medical devices and more particularly to electrical stimulation programming techniques.

BACKGROUND

Neurostimulation, also referred to as neuromodulation, has been proposed as a therapy for a number of conditions. Examples of neurostimulation include Spinal Cord Stimulation (SCS), Deep Brain Stimulation (DBS), Peripheral Nerve Stimulation (PNS), and Functional Electrical Stimulation (FES). Implantable neurostimulation systems have been applied to deliver such a therapy. An implantable neurostimulation system may include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system. An external programming device is used to program the implantable neurostimulator with stimulation parameters controlling the delivery of the neurostimulation energy.

In one example, the neurostimulation energy is delivered in the form of electrical neurostimulation pulses. The delivery is controlled using stimulation parameters that specify spatial (where to stimulate), temporal (when to stimulate), and informational (patterns of pulses directing the nervous system to respond as desired) aspects of a pattern of neurostimulation pulses. Many current neurostimulation systems are programmed to deliver periodic pulses with one or a few uniform waveforms continuously or in bursts. However, the human nervous systems use neural signals having much more sophisticated patterns to communicate various types of information, including sensations of pain, pressure, temperature, etc. The nervous system may interpret an artificial stimulation with a simple pattern of stimuli as an unnatural phenomenon, and respond with an unintended and undesirable sensation and/or movement. For example, some neurostimulation therapies are known to cause paresthesia and/or vibration of non-targeted tissue or organ.

Recent research has shown that the efficacy and efficiency of certain neurostimulation therapies can be improved, and their side-effects can be reduced, by using patterns of neurostimulation pulses that emulate natural patterns of neural signals observed in the human body. While modern electronics can accommodate the need for generating such sophisticated pulse patterns, the capability of a neurostimulation system depends on its post-manufacturing programmability to a great extent. For example, a sophisticated pulse pattern may only benefit a patient when it is customized for that patient, and stimulation patterns predetermined at the time of manufacturing may substantially limit the potential for the customization. Such customization may be performed at least in part by a user such as a physician or other caregiver with the patient in a clinical setting.

SUMMARY

In an example, this disclosure is directed to a machine-implemented method of providing therapy to a patient using a plurality of electrodes implanted within the patient, the method comprising receiving, via a programmer for an electrical stimulator, user input that at least partially defines a neuromodulation field to provide the therapy; based on the received user input, determining a subset of the plurality of electrodes and current distributions for the subset to generate the field; comparing an electrode limit to a number of electrodes in the determined subset and eliminating at least one of the number of electrodes in the determined subset based on the comparison to provide a reduced subset of the electrodes; and redistributing current associated with the at least one eliminated electrode to at least one of the electrodes in the reduced subset of electrodes.

In another example, this disclosure is directed to a system of providing therapy to a patient using a plurality of electrodes implanted within the patient, the system comprising: a programmer for an electrical stimulator, the programmer including: a user interface configured to receive user input that at least partially defines a neuromodulation field to provide the therapy; and at least one controller in communication with the user interface, the at least one controller configured to determine a subset of the plurality of electrodes and current distributions for the subset to generate the field based on the received user input; a comparator configured to compare an electrode limit to a number of electrodes in the determined subset and eliminate at least one of the number of electrodes in the determined subset based on the comparison to provide a reduced subset of the electrodes, and the at least one controller configured to redistribute current associated with the at least one eliminated electrode to at least one of the electrodes in the reduced subset of electrodes.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses various techniques that can allow a user to simplify a potentially complicated anode/cathode configuration during a programming session of an electrical stimulator. After a user has at least partially defined a neurostimulation field to provide therapy to a patient, a programming device can determine a plurality of electrodes, including anode(s) and cathode(s), and associated current distributions in order to generate the neurostimulation field. The programming device, however, may not prioritize power savings and can often assign small amounts of current to various anodes and cathodes. These small currents can be undesirable from a power perspective.

Various techniques of this disclosure can include a "simplify programming" feature that can eliminate one or more of the anodes or cathodes determined by the programming devices, particularly those associated with small currents. By eliminating one or more electrodes associated with small currents, the techniques of this disclosure can significantly reduce the power consumption of the implantable neurostimulator. In addition, the "simplify programming" feature can reduce the amount of time that clinicians spend programming the implantable neurostimulator during programming sessions.

In various embodiments, the present subject matter may be implemented using a combination of hardware and software designed to provide users such as clinical researchers, physicians or other caregivers with the ability to create custom waveforms and patterns in an effort to increase therapeutic efficacy and/or patient satisfaction for neurostimulation therapies, including but not being limited to SCS and DBS therapies. While neurostimulation is specifically discussed as an example, the present subject matter may apply to any therapy that employs stimulation pulses of electrical or other forms of energy.

Figure 1:
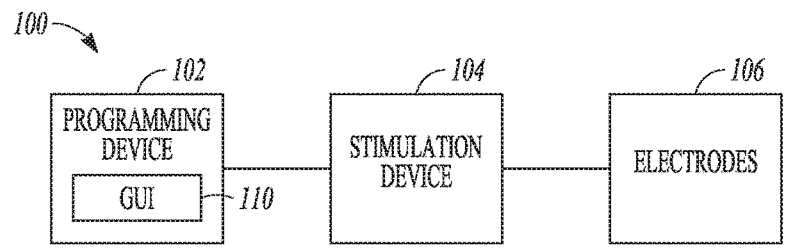
FIG. 1 illustrates an embodiment of a neurostimulation system.

FIG. 1 illustrates an embodiment of a neurostimulation system 100. System 100 includes electrodes 106, a stimulation device 104, and a programming device 102. Electrodes 106 are configured to be placed on or near one or more neural targets in a patient. Stimulation device 104 is configured to be electrically connected to electrodes 106 and deliver neurostimulation energy, such as in the form of electrical pulses, to the one or more neural targets though electrodes 106. The delivery of the neurostimulation is controlled by using a plurality of stimulation parameters, such as stimulation parameters specifying a pattern of the electrical pulses and a selection of electrodes through which each of the electrical pulses is delivered.

In various embodiments, at least some parameters of the plurality of stimulation parameters are programmable by a user, such as a physician or other caregiver who treats the patient using system 100. Programming device 102 provides the user with accessibility to the user-programmable parameters. In various embodiments, programming device 102 is configured to be communicatively coupled to stimulation device 104 via a wired or wireless link.

In various embodiments, programming device 102 includes a graphical user interface (GUI) 110 that allows the user to set and/or adjust values of the user-programmable parameters by creating and/or editing graphical representations of various waveforms. Such waveforms may include, for example, the waveform of a pattern of neurostimulation pulses to be delivered to the patient as well as individual waveforms that are used as building blocks of the pattern of neurostimulation pulses. Examples of such individual waveforms include pulses, pulse groups, and groups of pulse groups, as further discussed below. The user may also be allowed to define an electrode selection specific to each individually defined waveform.

The user can input one or more parameters using the GUI 110, for example, that at least partially define a neurostimulation field. Example parameters that can be of interest include, but are not limited to the following: amplitude, pulse width, frequency, total charge injected per unit time, cycling (e.g., on/off time), pulse shape, number of phases, phase order, interphase time, charge balance, ramping, as well as spatial variance (e.g., electrode configuration changes over time).

As described in more detail below, the GUI 110 of the programmer 102 can receive user input that at least partially defines a neuromodulation field to provide the neurostimulation therapy to a patient. Based on the received user input, the programmer 102 can determine a subset of available electrodes and current distributions for the subset to generate the field.

Using the "simplified programming" features of this disclosure, the programmer 102 can compare an electrode limit to the number of electrodes in the determined subset and eliminate at least one of the number of electrodes in the determined subset based on the comparison to provide a reduced subset of the electrodes. Then, the programmer 102 can redistribute the current associated with the eliminated electrode(s) to at least one of the electrodes in the reduced subset of electrodes.

Portions of the stimulation device 104, e.g., implantable medical device, or the programming device 102 can be implemented using hardware, software, or any combination of hardware and software. Portions of the stimulation device 104 or the programming device 102 may be implemented using an application-specific circuit that can be constructed or configured to perform one or more particular functions, or can be implemented using a general-purpose circuit that can be programmed or otherwise configured to perform one or more particular functions. Such a general-purpose circuit can include a microprocessor or a portion thereof, a microcontroller or a portion thereof, or a programmable logic circuit, or a portion thereof. The system 100 could include a subcutaneous medical device (e.g., subcutaneous ICD, subcutaneous diagnostic device), wearable medical devices patch based sensing device), or other external medical devices.

Figure 2:
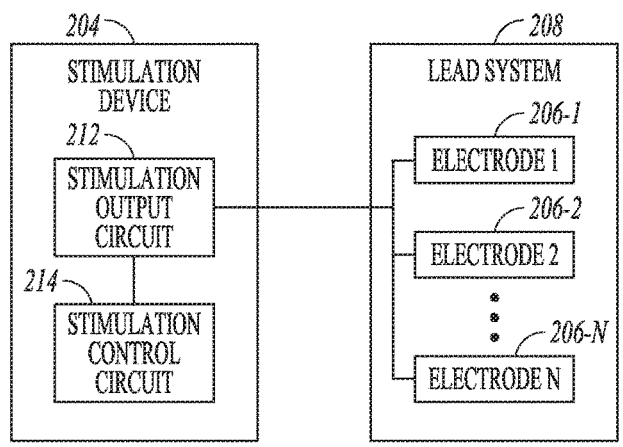
FIG. 2 illustrates an embodiment of a stimulation device and a lead system, such as may be implemented in the neurostimulation system of FIG. 1.

FIG. 2 illustrates an embodiment of a stimulation device 204 and a lead system 208, such as may be implemented in neurostimulation system 100. Stimulation device 204 represents an embodiment of stimulation device 104 and includes a stimulation output circuit 212 and a stimulation control circuit 214. Stimulation output circuit 212 produces and delivers neurostimulation pulses, including the user-defined customized neurostimulation waveform received using the GUI 110. Stimulation control circuit 214 controls the delivery of the neurostimulation pulses using the plurality of stimulation parameters, which specifies a pattern of the neurostimulation pulses. Lead system 208 includes one or more leads each configured to be electrically connected to stimulation device 204 and a plurality of electrodes 206 distributed in the one or more leads. The plurality of electrodes 206 includes electrode 206-1, electrode 206-2, . . . electrode 206-N, each a single electrically conductive contact providing for an electrical interface between stimulation output circuit 212 and tissue of the patient, where N≥2. The neurostimulation pulses are each delivered from stimulation output circuit 212 through a set of electrodes selected from electrodes 206. In various embodiments, the neurostimulation pulses may include one or more individually defined pulses, and the set of electrodes may be individually definable by the user for each of the individually defined pulses.

In various embodiments, the number of leads and the number of electrodes on each lead depend on, for example, the distribution of target(s) of the neurostimulation and the need for controlling the distribution of electric field at each target. In one embodiment, lead system 208 includes 2 leads each having 8 electrodes. In other embodiments, the lead system 208 can include a paddle with 32 electrode and shown in NG. 7, for example.

Figure 3:
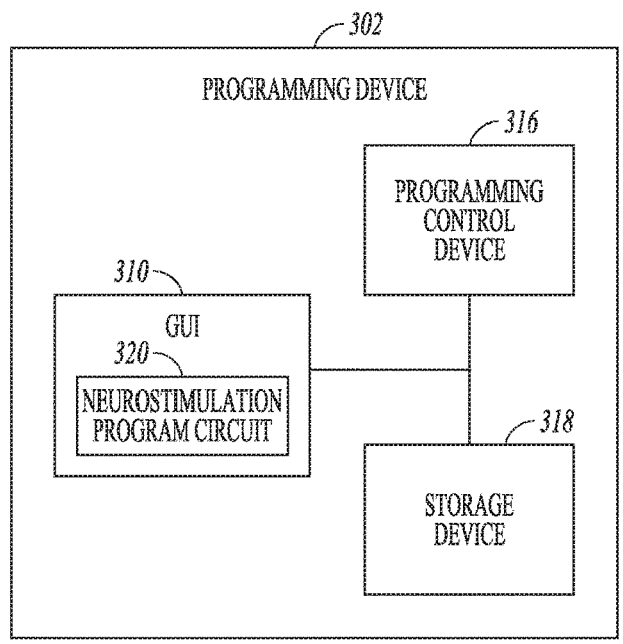
FIG. 3 illustrates an embodiment of a programming device, such as may be implemented in the neurostimulation system of FIG. 1.

FIG. 3 illustrates an embodiment of a programming device 302, such as may be implemented in neurostimulation system 100. Programming device 302 represents an embodiment of programming device 102 and includes a storage device 318, a programming control circuit 316, and a GUI 310.

Programming control circuit 316 generates the plurality of stimulation parameters that controls the delivery of the neurostimulation pulses according to the pattern of the neurostimulation pulses. GUI 310 represents an embodiment of GUI 110.

In various embodiments, GUI 310 includes a neurostimulation program circuit 320 that creates neurostimulation programs and schedules delivery of the neurostimulation programs. In various embodiments, neurostimulation program circuit 320 allows the user to create each neurostimulation program, including a therapeutic neurostimulation field. In some examples, the GUI 310 can receive user input to initiate the "simplify programming" techniques of this disclosure, which are described in more detail below.

In various embodiments, neurostimulation program circuit 320 allows the user to schedule delivery of each neurostimulation program, such as by specifying delivery time for certain building blocks and a frequency at which the program is delivered. In various embodiments, neurostimulation program circuit 320 allows the user to create each building block or program using one or more waveforms stored in storage device 318 as templates. In various embodiments, neurostimulation program circuit 320 allows each newly created building block or program to be saved as additional waveforms stored in storage device 318.

In one embodiment, GUI 310 includes a touchscreen. In various embodiments, GUI 310 includes any type of presentation device, such as interactive or non-interactive screens, and any type of user input device that allows the user to edit the waveforms or building blocks and schedule the programs, such as touchscreen, keyboard, keypad, touchpad, trackball, joystick, and mouse. In various embodiments, circuits of neurostimulation 100, including its various embodiments discussed in this document, may be implemented using a combination of hardware and software. For example, the circuit of GUI 100, stimulation control circuit 214, and programming control circuit 316, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 4:
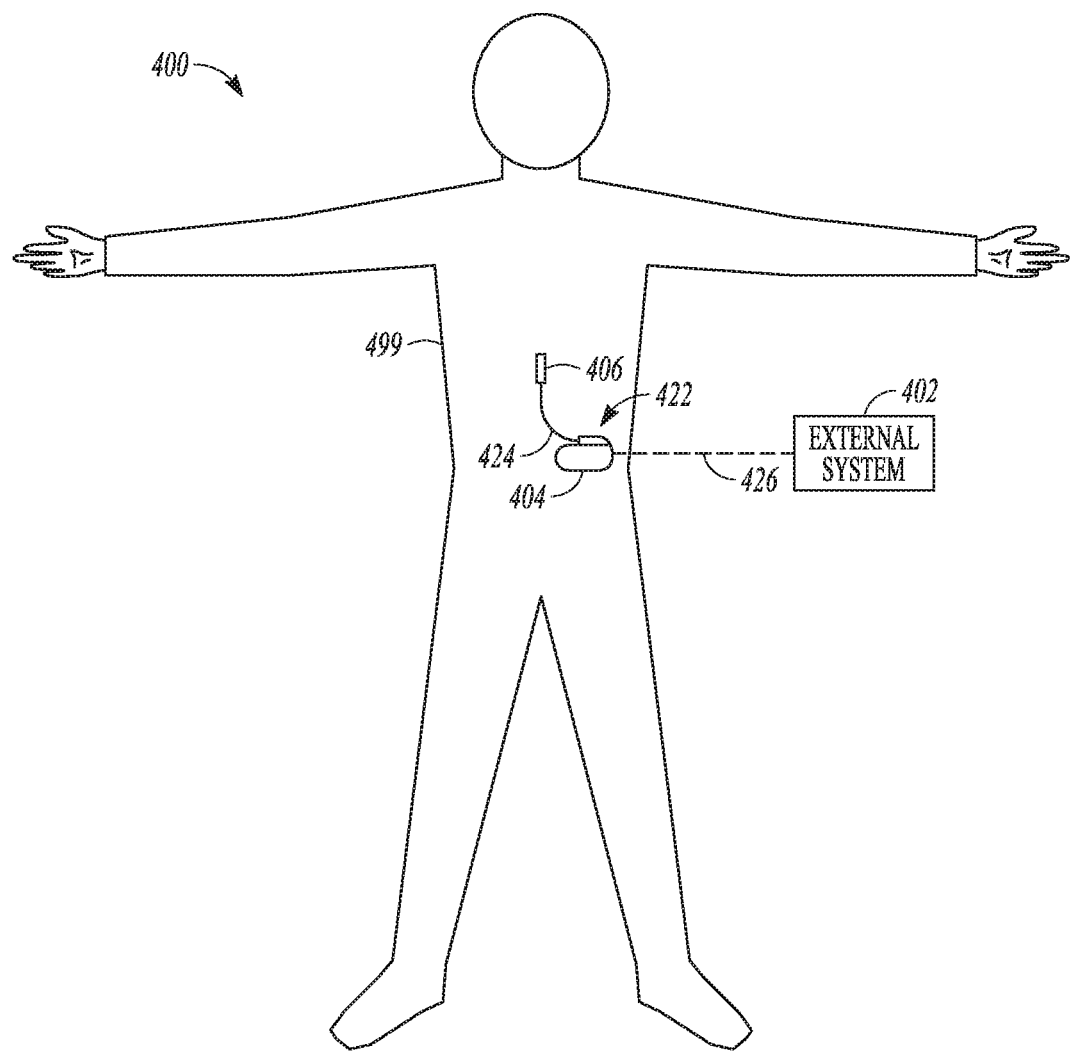
FIG. 4 illustrates an implantable neurostimulation system and portions of an environment in which the system may be used.

FIG. 4 illustrates an implantable neurostimulation system 400 and portions of an environment in which system 400 may be used. System 400 includes an implantable system 422, an external system 402, and a telemetry link 426 providing for wireless communication between implantable system 422 and external system 402. Implantable system 422 is illustrated in FIG. 4 as being implanted in the patient's body 499.

Implantable system 422 includes an implantable stimulator (also referred to as an implantable pulse generator, or IPG) 404, a lead system 424, and electrodes 406, which represent an embodiment of stimulation device 204, lead system 208, and electrodes 206, respectively. External system 402 represents an embodiment of programming device 302.

In various embodiments, external system 402 includes one or more external (non-implantable) devices each allowing the user and/or the patient to communicate with implantable system 422. In some embodiments, external 402 includes a programming device intended for the user to initialize and adjust settings for implantable stimulator 404 and a remote control device intended for use by the patient. For example, the remote control device may allow the patient to turn implantable stimulator 404 on and off and/or adjust certain patient-programmable parameters of the plurality of stimulation parameters.

Figure 5:
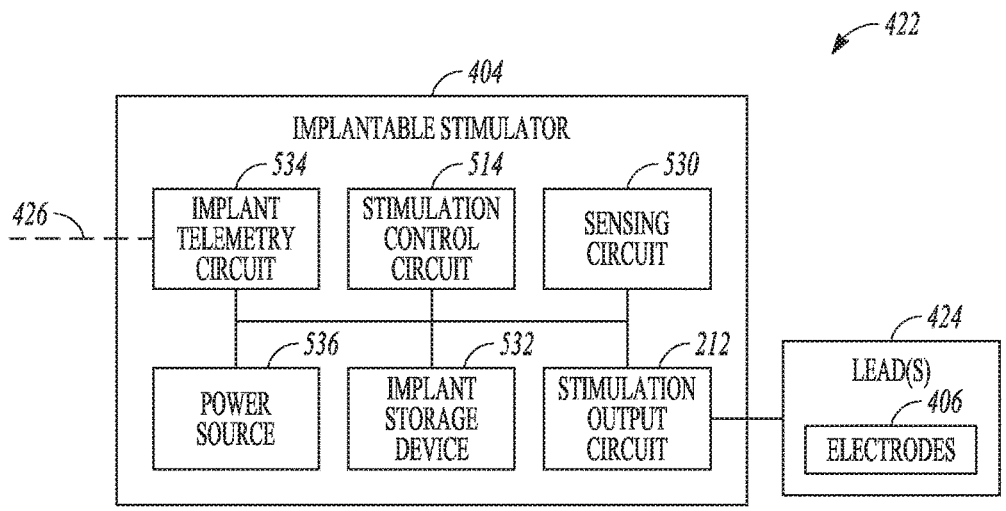
FIG. 5 illustrates an embodiment of an implantable stimulator and one or more leads of an implantable neurostimulation system, such as the implantable system of FIG. 4.

FIG. 5 illustrates an embodiment of implantable stimulator 404 and one or more leads 424 of an implantable neurostimulation system, such as implantable system 422. Implantable stimulator 404 may include a sensing circuit 530 that is optional and required only when the stimulator has a sensing capability, stimulation output circuit 212, a stimulation control circuit 514, an implant storage device 532, an implant telemetry circuit 534, and a power source 536. Sensing circuit 530, when included and needed, senses one or more physiological signals for purposes of patient monitoring and/or feedback control of the neurostimulation. Examples of the one or more physiological signals includes neural and other signals each indicative of a condition of the patient that is treated by the neurostimulation and/or a response of the patient to the delivery of the neurostimulation.

Stimulation output circuit 212 is electrically connected to electrodes 406 through lead 424, and delivers each of the neurostimulation pulses through a set of electrodes selected from electrodes 406. Stimulation output circuit 212 can generating and delivery the customized first neurostimulation waveform (input by the user and compared to existing neurostimulation waveforms) to an anatomical target of a patient.

Stimulation control circuit 514 represents an embodiment of stimulation control circuit 214 and controls the delivery of the neurostimulation pulses using the plurality of stimulation parameters specifying the pattern of the neurostimulation pulses. In one embodiment, stimulation control circuit 514 controls the delivery of the neurostimulation pulses using the one or more sensed physiological signals. Implant telemetry circuit 534 provides implantable stimulator 404 with wireless communication with another device such as a device of external system 402, including receiving values of the plurality of stimulation parameters from external system 402. Implant storage device 532 stores values of the plurality of stimulation parameters.

Power source 536 provides implantable stimulator 404 with energy for its operation. In one embodiment, power source 536 includes a battery. In one embodiment, power source 536 includes a rechargeable battery and a battery charging circuit for charging the rechargeable battery. Implant telemetry circuit 534 may also function as a power receiver that receives power transmitted from external system 402 through an inductive couple.

In various embodiments, sensing circuit 530 (if included), stimulation output circuit 212, stimulation control circuit 514, implant telemetry circuit 534, implant storage device 532, and power source 536 are encapsulated in a hermetically sealed implantable housing. In various embodiments, lead(s) 424 are implanted such that electrodes 406 are places on and/or around one or more targets to which the neurostimulation pulses are to be delivered, while implantable stimulator 404 is subcutaneously implanted and connected to lead(s) 424 at the time of implantation.

Figure 6:
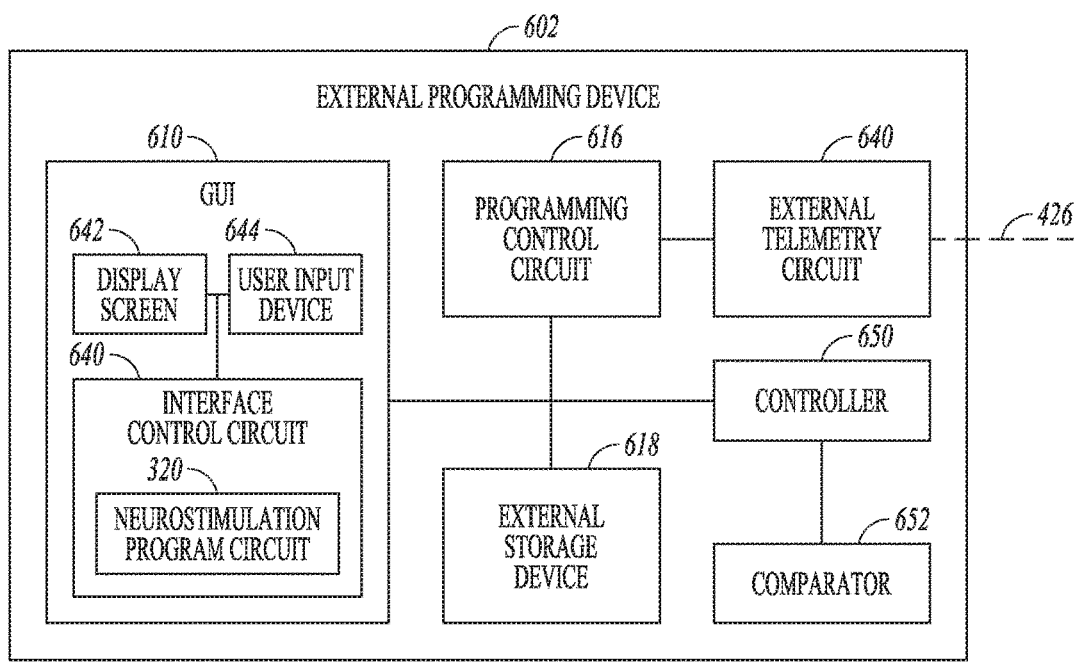
FIG. 6 illustrates an embodiment of an external programming device of an implantable neurostimulation system, such as the external system of FIG. 4.

FIG. 6 illustrates an embodiment of an external programmer 602 of an implantable neurostimulation system, such as external system 402. External programmer 602 represents an embodiment of programming device 302, and includes an external telemetry circuit 640, an external storage device 618, a programming control circuit 616, a GUI 610, a controller 650, and a comparator 652.

External telemetry circuit 640 provides external programmer 602 with wireless communication with another device such as implantable stimulator 404 via telemetry link 426, including transmitting the plurality of stimulation parameters to implantable stimulator 404. In one embodiment, external telemetry circuit 640 also transmits power to implantable stimulator 404 through the inductive couple.

External storage device 618 stores a plurality of existing neurostimulation waveforms, including individually definable waveforms each selectable for use as a portion of the pattern of the neurostimulation pulses. In various embodiments, each waveform of the plurality of individually definable waveforms includes one or more pulses of the neurostimulation pulses, and may include one or more other waveforms of the plurality of individually definable waveforms. Examples of such waveforms include pulses, pulse blocks, pulse trains, and train groupings, and programs. The existing waveforms stored in the external storage device 618 can be definable at least in part by one or more parameters including, but not limited to the following: amplitude, pulse width, frequency, electrode configurations, total charge injected per unit time, cycling (e.g., on/off time), pulse shape, number of phases, phase order, interphase time, charge balance, and ramping.

External storage device 618 also stores a plurality of individually definable fields. Each waveform of the plurality of individually definable waveforms is associated with one or more fields of the plurality of individually definable fields. Each field of the plurality of individually definable fields is defined by one or more electrodes of the plurality of electrodes through which a pulse of the neurostimulation pulses is delivered and a current distribution of the pulse over the one or more electrodes.

Programming control circuit 616 represents an embodiment of programming control circuit 316 and generates the plurality of stimulation parameters, which is to be transmitted to implantable stimulator 404, based on the pattern of the neurostimulation pulses. The pattern is defined using one or more waveforms selected from the plurality of individually definable waveforms stored in external storage device 618. In various embodiment, programming control circuit 616 checks values of the plurality, of stimulation parameters against safety rules to limit these values within constraints of the safety rules. In one embodiment, the safety rules are heuristic rules.

GUI 610 represents an embodiment of user interface 310 and allows the user to define the pattern of neurostimulation pulses and perform various other monitoring and programming tasks. GM 610 includes a display screen 642, a user input device 644, and an interface control circuit 640. Display screen 642 may include any type of interactive or non-interactive screens, and user input device 644 may include any type of user input devices that supports the various functions discussed in this document, such as touchscreen, keyboard, keypad, touchpad, trackball, joystick, and mouse. In one embodiment, GUI 610 includes an interactive screen that displays a graphical representation of a stimulation waveform and allows the user to adjust the waveform by graphically editing the waveform and/or various building blocks of the waveform. GUI 610 may also allow the user to perform any other functions discussed in this document where graphical editing is suitable as may be appreciated by those skilled in the art.

Interface control circuit 640 controls the operation of GUI 610 including responding to various inputs received by user input device 644 and defining the one or more stimulation waveforms. Interface control circuit 640 includes neurostimulation control circuit 320.

In various embodiments, external programming device 602 has operation modes including a composition mode and a real-time programming mode. Under the composition mode (also known as the pulse pattern composition mode), GUI 610 is activated, while programming control circuit 616 is inactivated. Programming control circuit 616 does not dynamically update values of the plurality of stimulation parameters in response to any change in the one or more stimulation waveforms. Under the real-time programming mode, both GUI 610 and programming control circuit 616 are activated. Programming control circuit 616 dynamically updates values of the plurality of stimulation parameters in response to changes in the set of one or more stimulation waveforms, and transmits the plurality of stimulation parameters with the updated values to implantable stimulator 404.

The controller 650 can be a microprocessor that communicates with the external telemetry circuit 640, the external storage device 618, the programming control circuit 616, the GUI 610, the comparator 652 via a bidirectional data bus. The controller 650 can be implemented by other types of logic circuitry (e.g., discrete components or programmable logic arrays) using a state machine type of design. As used in this disclosure, the term "circuitry" should be taken to refer to either discrete logic circuitry, firmware, or to the programming of a microprocessor. The comparator 652 can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals.

In accordance with various techniques of this disclosure, the controller 650 can receive, via GUI 610 for example, user input that at least partially defines a neurostimulation field to provide therapy to a patient. After having received the user input at least partially defining the neurostimulation field, the controller 650 can execute instructions that cause the programming control circuit 616 to generate a plurality of stimulation parameters to generate the neurostimulation field. In particular, the programming control circuit 316 can determine 1) a subset of electrodes from the number of available electrodes on the lead(s) and 2) current distributions associated with electrodes in the subset.

Using the "simply programming" techniques of this disclosure, the controller 650, using comparator 652, can compare an electrode limit to the number of electrodes in the electrode subset determined by the programming control circuit 616. In some example implementations, the electrode limit can be a pre-programmed limit stored in the programming device 602, e.g., in external storage device 618, in other example implementations, the programming device 602 can receive a user selection, e.g., using GUI 610, that allows a user to select the electrode limit.

For example, a user may determine that a bipolar electrode configuration is desirable and set an electrode limit of 2, e.g., either pre-programmed or when prompted. In another example, a user may determine that a tripolar electrode configuration is desirable and set an electrode limit of 3, e.g., either pre-programmed or when prompted. These electrode limits are examples. The user can select an electrode limit of more than 3 electrodes.

After comparing the electrode limit to the number of electrodes in the electrode subset determined by the programming control circuit 616, the controller 650 can execute instructions that eliminate at least one of the number of electrodes in the determined subset based on the comparison, thereby providing a reduced subset of the electrodes. In some example configurations, the determined subset of the electrodes can include at least two anodic electrodes and at least two cathodic electrodes to provide the field. In such configurations, the controller 650 can eliminate one anodic electrode based on the anodic electrode having a lowest associated anodic current distribution for the subset and/or eliminate one cathodic electrode based on the cathodic electrode having a lowest associated cathodic current distribution for the subset. In other configurations, the controller 650 can eliminate more than one anodic electrode and/or cathode electrode.

After the controller 650 has eliminate the electrode(s) based on the comparison with the electrode limit, the controller 650 can redistribute the current associated with the eliminated electrode(s) to at least one of the electrodes in the reduced subset of electrodes For example, if the programming control circuit 616 determined that the desired neurostimulation field could be generated using 6 electrodes and the user had set an electrode limit of 2, the controller 650 can eliminate 4 electrodes and redistribute their respective currents amongst the two remaining electrodes.

Regarding redistribution of current, in some example implementations, the controller 650 can evenly redistribute a current distribution associated with an eliminated electrode having a first polarity, e.g., anodic, to the remaining electrodes having the first polarity, e.g., anodic. For example, if the eliminated electrode was an anode that had an associated current of 8 milliamps and 4 anodes remained, the 8 milliamps would be evenly distributed such that the associated current of each of the remaining 4 anodes increased by 2 milliamps.

In other example implementations, the controller 650 can proportionally redistribute a current distribution associated with the eliminated electrode having a first polarity, e.g., anodic, to the remaining electrodes having the first polarity, e.g., anodic. For example, if the eliminated electrode was an anode that had an associated current of 8 milliamps and 3 anodes remained, the 8 milliamps would be proportionately distributed amongst the 3 anodes based on their current distributions. Assume that a first one of the 3 anodes was configured to deliver 50% of the anodic current, a second one of the 3 anodes was configured to deliver 25%, and a third one of the 3 anodes was configured to deliver the remaining 25%, then the 8 milliamps would be redistributed such that the first anode current increased by 4 milliamps and the current associated with each of the second and third anodes increased by 2 milliamps. Various examples of electrode elimination and current redistribution are shown and described in detail below with respect to FIGS. 7-12.

Following redistribution of the current, the programming device 602 can configure the implantable stimulator, e.g., implantable stimulator 404 of FIG. 5, to convey electrical current to the electrodes remaining in the determined subset of electrodes in accordance with the redistributed current distribution, thereby providing therapy to the patient.

As mentioned above, various techniques of this disclosure, in particular the elimination of one or more electrodes of a determined subset of electrodes for delivering a neurostimulation field, can substantially reduce power consumption and therefore extend battery life. These techniques can be particularly useful when high-frequency neurostimulation is delivered, which can consume more power than low-frequency neurostimulation.

High-frequency neurostimulation can be used to deliver sub-perception therapy. Sub-perception therapy can be therapeutically effective to treat pain, for example, but the patient does not perceive paresthesia, e.g., the patient does not sense the delivery of the modulation field. Some patients prefer not to perceive paresthesia, particularly at certain times of the day, e.g., bedtime.

The "simplify programming" techniques described above can additionally or alternatively include techniques to simplify programming of sub-perception therapy. For example, a user can perform a mapping procedure that can include receiving user input, e.g., using GUI 610 of programming device 602, that at least partially defines a neuromodulation field to provide the neurostimulation therapy. In response, the programming control circuit 316 can generate the stimulation parameters, which can be transmitted to implantable stimulator 404. Using the programming device 602, e.g., the GUI 610, the user can modify the neuromodulation field to cause paresthesia to cover an area of pain experienced by the patient, e.g., using the patient's feedback to assist in modifying the field.

In some example implementations, once the user has determined that the field has covered the area of pain, the user can provide input to the programming device 602, e.g., selecting an icon using the GUI 610, to eliminate one or more electrodes described above). In addition, in a sub-perception therapy "simplify programming" embodiment, the user can provide input to the programming device 602, e.g., selecting an icon using the GUI 610, that modifies the neurostimulation field to not cause the patient to perceive paresthesia. For example, the programming device 602 can, in response to the user input, 1) reduce an amplitude of the neurostimulation by a percentage, such as 20-80%, or to a specific value, for example; 2) adjust a pulse width of the neurostimulation by a percentage or to a specific value, for example; 3) increase the frequency of the neurostimulation to between 300 Hertz (Hz) and 10,000 Hz, where 40 Hz-120 Hz is generally considered to cause paresthesia and 300 Hz and above is generally considered to be the range sub-perception frequencies. By way of specific example, the programming device 602 can reduce the amplitude by 50%, modify the pulse width to 130 microseconds, and set the frequency at 1200 Hz to provide a sub-perception therapy.

Figure 7:
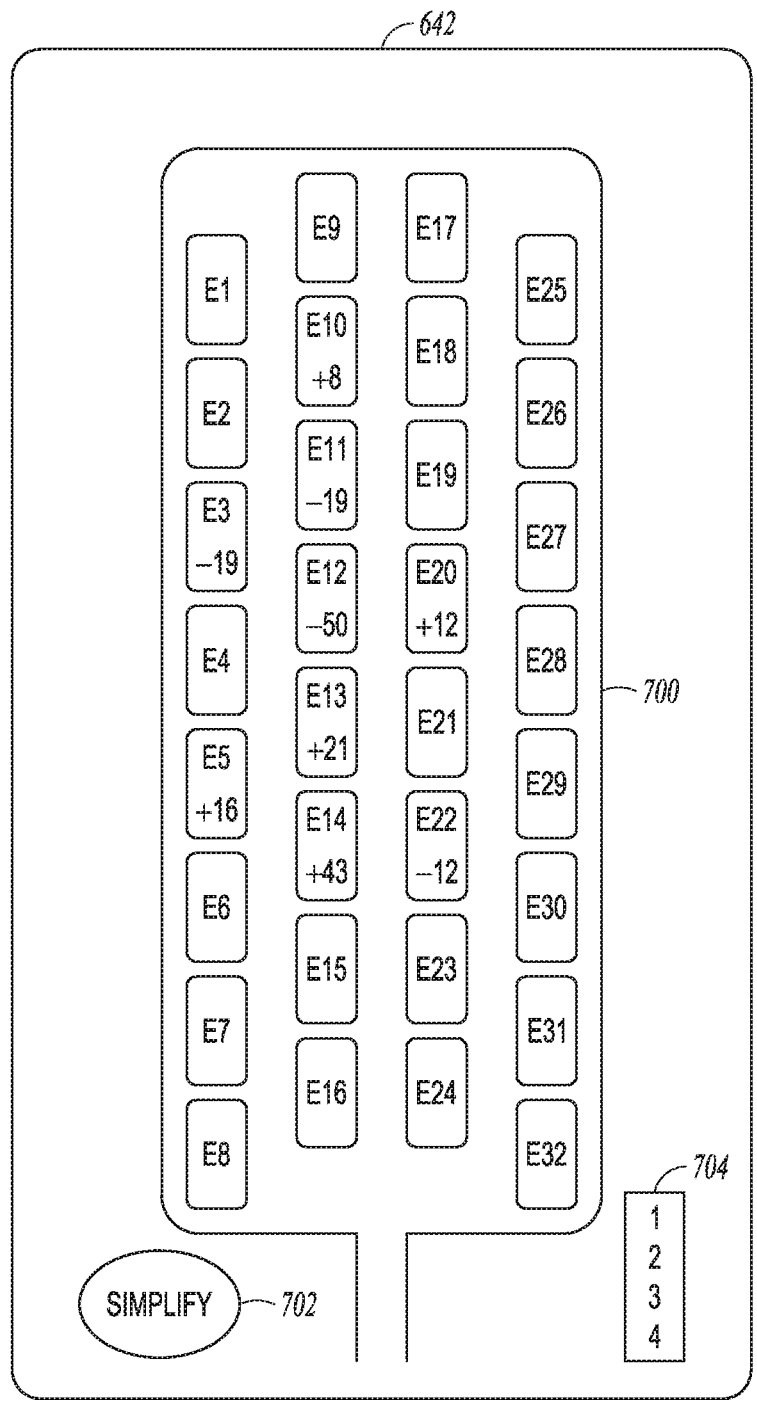
FIG. 7 is a plan view of an example of a programming screen generated by the programming device of FIG. 6 and depicting the lead used in the system of FIG. 4.

FIG. 7 is a plan view of an example of a programming screen generated by the programming device of FIG. 6 and depicting the lead 424 used in the system of FIG. 4. Although the lead shown in FIG. 7 is a paddle lead, the disclosure is not so limited. In addition to paddle leads, the techniques of this disclosure are applicable to any lead system, including one or more percutaneous leads, for example. Example percutaneous leads include 1×4 percutaneous leads, 1×8 percutaneous leads, 1×16 percutaneous leads, and combinations of 1×4 percutaneous leads, 1×8 percutaneous, and 1×16 percutaneous leads, such as two 2×8 percutaneous leads, as shown in FIG. 4 of commonly assigned U.S. Pat. No. 8,594,797 to Lee et al., which is incorporated by reference herein in its entirety. The display screen 642, e.g., of the programming device 602 of FIG. 6, depicts a graphical representation 700 of the paddle lead 424 of FIG. 4 having a plurality of electrodes E1-E32, for example.

In FIG. 7, the programming device, e.g., programming device 602, has already received user input that at least partially defines a neuromodulation field to provide a neurostimulation therapy and, based on the received user input, determined a subset of the plurality of electrodes and current distributions for the subset to generate the field. The display screen 642 displays the determined current distributions for the subset. As seen in FIG. 7, the programming device determined that 9 electrodes (5 anodes and 4 cathodes) can generate the field.

Using the techniques of this disclosure, the user can simplify this example of a complicated anode/cathode configuration. In some examples, the user can provide input to the programming device 602, e.g., using GUI 610, to reduce the number of electrodes in the determined subset. For example, the GUI 610 can display a "simplify" icon 702, which the user can select if simplification is desired. In response, the programming device 602 can compare an electrode limit to a number of electrodes in the determined subset and eliminate at least one of the number of electrodes in the determined subset based on the comparison to provide a reduced subset of the electrodes.

In some example implementations, the electrode limit, e.g., a total number of anodes and cathodes to generate the field, can be previously specified and stored in the storage device 618 and used by the controller 650 for comparison. In other example implementations, the GM 610 can allow the user to select the electrode limit. For example, the GUI 610 can display a graphical input icon 704, e.g., scroll wheel or other graphical input icon, that displays an electrode limit selectable by the user or allows a user to directly input the number of electrodes in electrode limit.

In the example shown in FIG. 7, electrode E10 has an associated anodic current distribution of 8, which is the lowest associated anodic current distribution for the displayed subset of 9 electrodes. By selecting the "simplify" icon 702, the controller 650 can compare the number of electrodes in the determined subset (9 in this specific example), to the number in an electrode limit, e.g., 8 electrodes, and eliminate electrode E10. Then, the controller 650 can redistribute the current associated with the eliminated anode E10 to the remaining anodes in the reduced subset of electrodes (anodes E5, E13, E14, and E20 in FIG. 7). Examples of the redistribution are shown in FIGS. 8 and 9.

Figure 8:
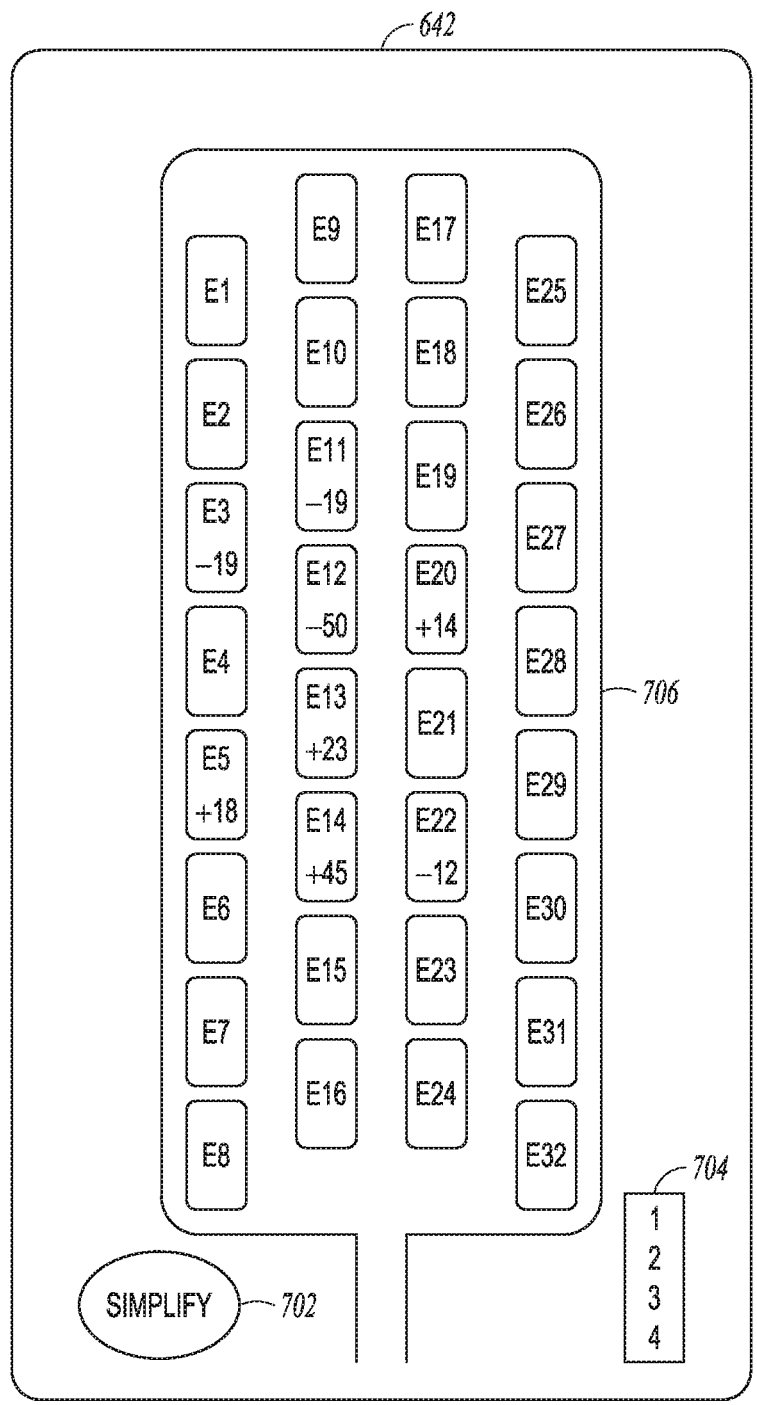
FIG. 8 is a plan view of an example of a programming screen generated by the programming device of FIG. 6 and depicting the lead used in the system of FIG. 4, following an even redistribution of current.

FIG. 8 is a plan view of an example of a programming screen generated by the programming device of FIG. 6 and depicting the lead 424 used in the system of FIG. 4, following an even redistribution of current. The display screen 642 depicts a graphical representation 706 of the lead of FIG. 7 after an anode has been eliminated and its associated current has been evenly redistributed to the remaining anodes.

In FIG. 8, controller 650 (of FIG. 6) has evenly redistributed the current distribution of 8 associated with the electrode E10 in FIG. 7 to the remaining anodes, namely anodes E5, E13, E14, and E20. In evenly redistributing the current associated with anode E10, the controller 650 can evenly divide the current distribution of 8 associated with anode E10 by the number of anodes (4) remaining in the subset. As seen in FIG. 8, anode E5 increases from 16 to 18, anode E13 increases from 21 to 23, anode E14 increases from 43 to 45, and anode E20 increases from 12 to 14. In this manner, the current associated with the one or more eliminated anodes can be divided by the number of anodes remaining in the subset and then distributed amongst those remaining anodes. Similarly, if one or more cathodes are eliminated, the current associated with the one or more eliminated cathodes can be divided by the number of cathodes remaining in the subset and then distributed amongst those remaining cathodes.

Figure 9:
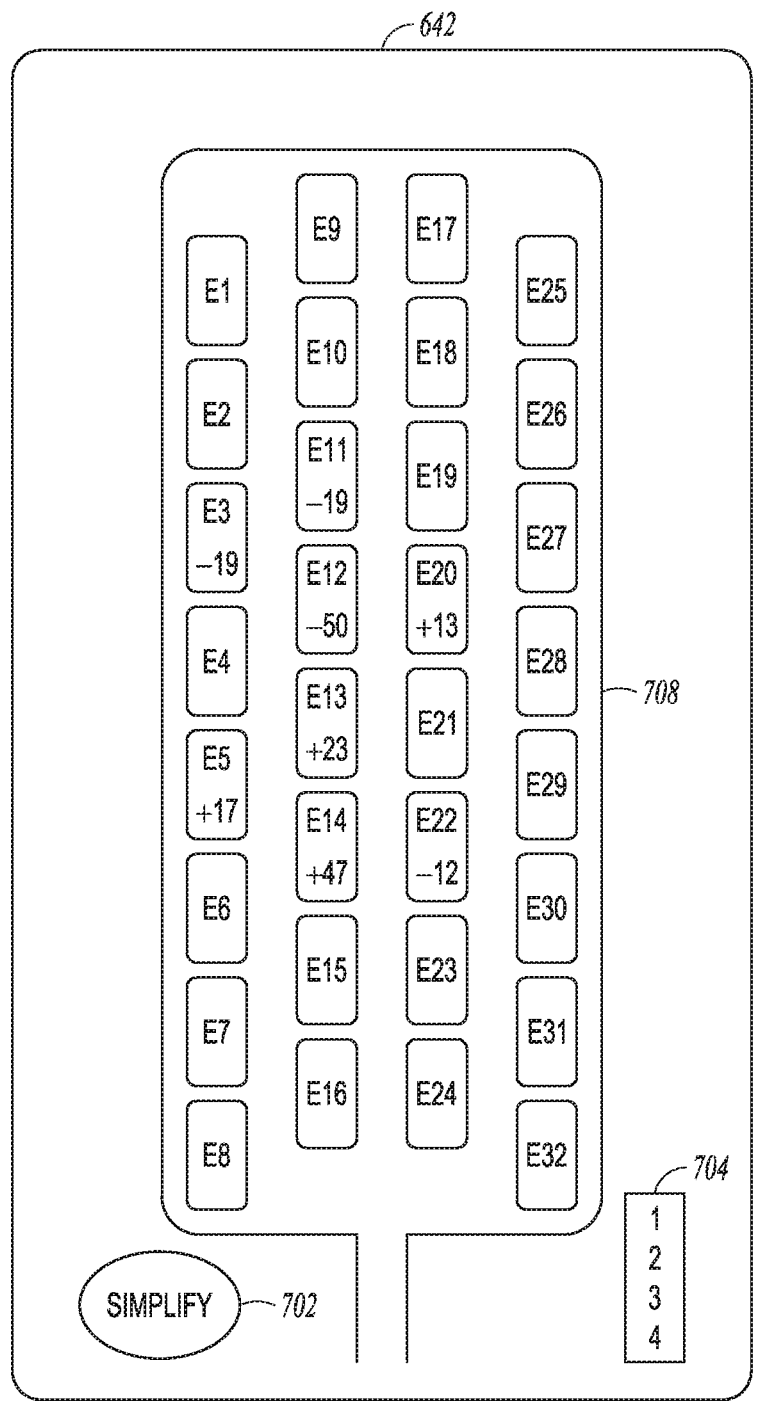
FIG. 9 is a plan view of an example of a programming screen generated by the programming device of FIG. 6 and depicting the lead used in the system of FIG. 4, following a proportional redistribution of current.

FIG. 9 is a plan view of an example of a programming screen generated by the programming device of FIG. 6 and depicting the lead 424 used in the system of FIG. 4, following a proportional redistribution of current. The display screen 642 depicts a graphical representation 708 of the lead of FIG. 7 after an anode has been eliminated and its associated current has been proportionally redistributed to the remaining anodes.

In FIG. 9, controller 650 (of FIG. 6) has proportionally redistributed the current distribution of 8 associated with the anode E10 in FIG. 7 to the remaining anodes, namely anodes E5, E13, E14, and E20. In proportionally redistributing the current associated with anode E10, the controller 650 can redistribute the current distribution of 8 associated with anode E10 based on the current distributions associated with the anodes remaining in the subset. As seen in FIG. 7, the anode E14 initially had a current distribution of 43, or 43% of the anodic current distribution. The controller 650 can determine that the anode E14 can proportionally receive about 43% of the current associated with the anode E10, thereby increasing from the current from 43 to about 47, as seen in FIG. 9.

As seen in FIG. 9, the anode E13 initially had a current distribution of 21, or 21% of the anodic current distribution. The controller 650 can determine that the anode E13 can proportionally receive about 21% of the current associated with the anode E10, thereby increasing the current from 21 to about 23. Similarly, the current associated with the anode E5 can increase from 16 to about 17, and the current associated with the anode E20 can increase from 12 to about 13.

Figure 10:
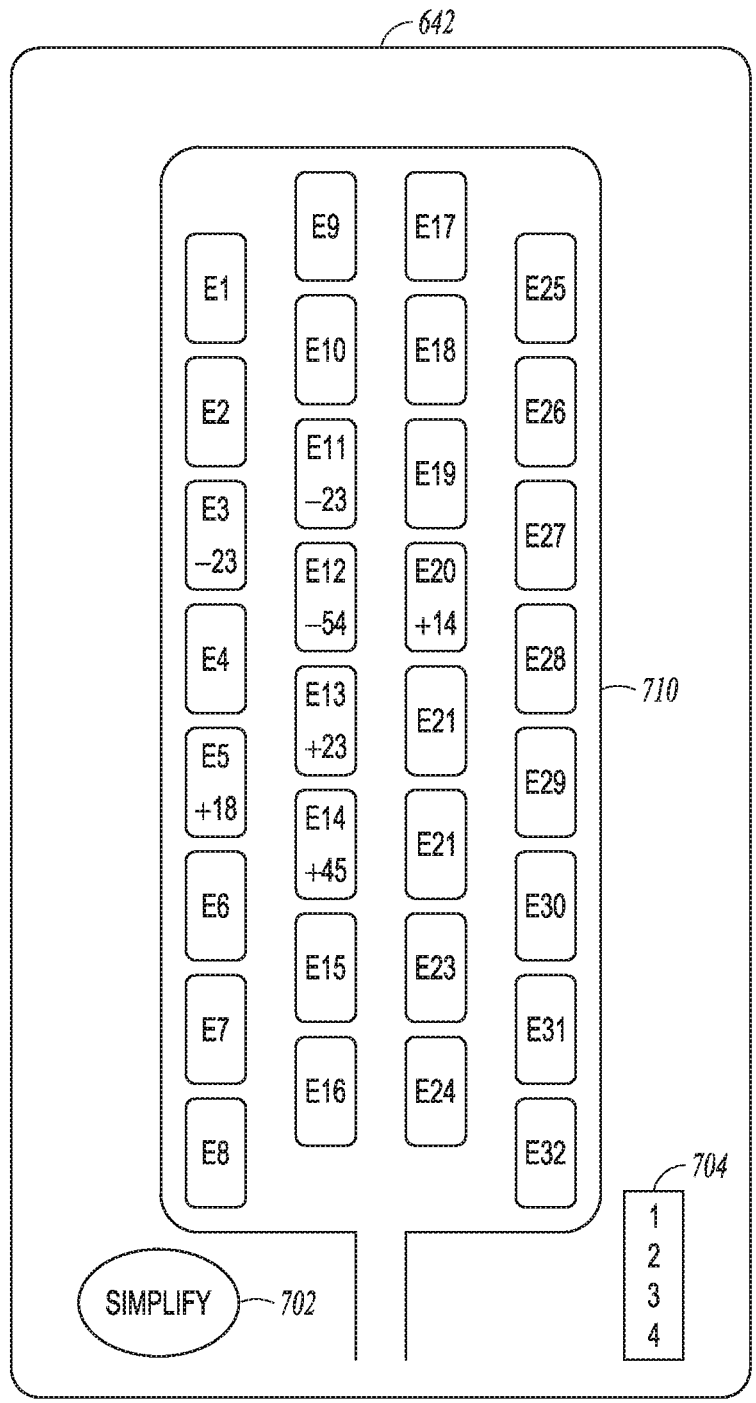
FIG. 10 is a plan view of an example of a programming screen generated by the programming device of FIG. 6 and depicting the lead used in the system of FIG. 4, following an even redistribution of current.

FIG. 10 is a plan view of an example of a programming screen generated by the programming device of FIG. 6 and depicting the lead 424 used in the system of FIG. 4, following an even redistribution of current. The display screen 642 depicts a graphical representation 710 of the lead of FIG. 7 after an anode (anode E10) and a cathode (cathode E22) have been eliminated and their associated current has been evenly redistributed to the remaining anodes and cathodes, respectively.

In FIG. 10, the controller 650 (of FIG. 6) has evenly redistributed the current distribution of 8 associated with the anode E10 in FIG. 7 to the remaining anodes, namely anodes E5, E13, E14, and E20. The redistribution was described above with respect to FIG. 7 and, for purposes of conciseness, will not be described in detail again.

The controller 650 (of FIG. 6) has also evenly redistributed the current distribution of 12 associated with the cathode E22 in FIG. 7 to the remaining cathodes, namely cathodes E3, E11, and E12. In evenly redistributing the current associated with anode E22, the controller 650 can evenly divide the current distribution of 12 associated with cathode E22 by the number of cathodes (3) remaining in the subset. As seen in FIG. 10, cathode E3 increases from 19 to 23, cathode E11 increases from 19 to 23, and cathode E12 increases from 50 to 54. In this manner, the complexity has been reduced from 9 electrodes (FIG. 7) to 7 electrodes (FIG. 10). Although only one anode and one cathode have been eliminated in FIG. 10, the techniques described above are applicable to multiple anodes and multiple cathodes.

Figure 11:
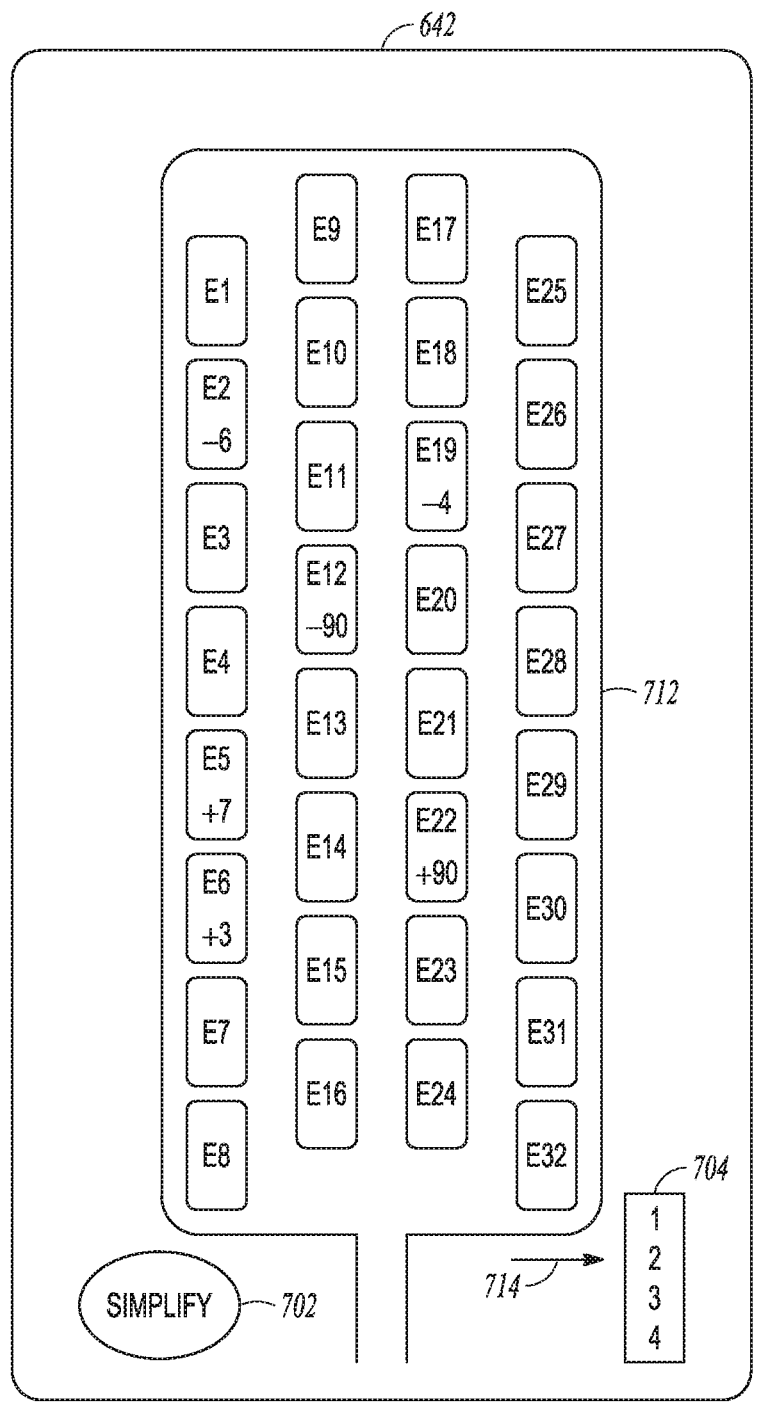
FIG. 11 is a plan view of another example of a programming screen generated by the programming device of FIG. 6 and depicting the lead used in the system of FIG. 4.

FIG. 11 is a plan view of another example of a programming screen generated by the programming device of FIG. 6 and depicting the lead 424 used in the system of FIG. 4. The display screen 642, e.g., of the programming device 602 of FIG. 6, depicts a graphical representation 712 of the paddle lead 424 of FIG. 4 having a plurality of electrodes E1-E32, for example. In FIG. 11, the programming device, e.g., programming device 602, has already received user input that at least partially defines a neuromodulation field to provide a neurostimulation therapy and, based on the received user input, determined a subset of the plurality of electrodes and current distributions for the subset to generate the field. The display screen 642 displays the determined current distributions for the subset. As seen in FIG. 11, the programming device determined that 6 electrodes (3 anodes and 3 cathodes) can generate the field.

Using the techniques of this disclosure, the user can simplify this example of a complicated anode/cathode configuration, which can reduce power consumption, particularly at higher frequencies. In the specific example shown in FIG. 11, the user has selected an electrode limit of 2 using the graphical input icon 704, e.g., scroll wheel or other graphical input icon, in order to reduce the number of electrodes (6) in the subset of electrodes initially determined by the controller 650 to 2 electrodes, e.g., a bipolar configuration.

Figure 12:
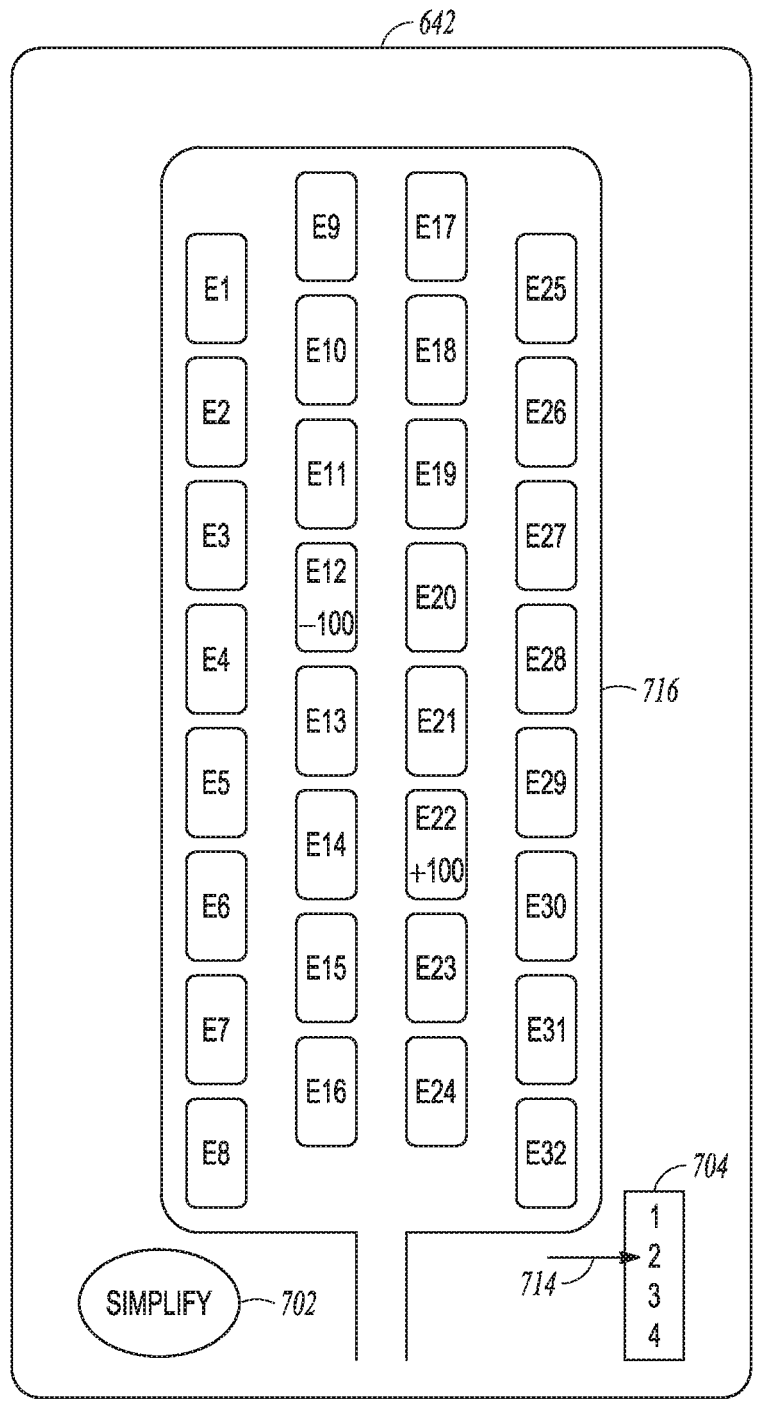
FIG. 12 is a plan view of another example of a programming screen generated by the programming device of FIG. 6 and depicting the lead used in the system of FIG. 4, following a redistribution of current.

The GUI 610 can display the "simplify" icon 702, which the user can select to simply the configuration. In response, the programming device 602 can compare the electrode limit of 2 to a number of electrodes in the determined subset (6) and eliminate 4 electrodes in the determined subset to provide a reduced subset of the electrodes. FIG. 12 depicts the resulting, simplified configuration.

FIG. 12 is a plan view of an example of a programming screen generated by the programming device of FIG. 6 and depicting the lead 424 used in the system of FIG. 4, following a redistribution of current. The display screen 642 depicts a graphical representation 716 of the lead of FIG. 11 after two anodes (anodes E5, E6) and two cathodes (cathodes E2, E19) have been eliminated and their associated current has been redistributed to the remaining anode E22 and cathode E12, respectively.

In FIG. 12, the controller 650 (of FIG. 6) has redistributed the anodic current of 7 associated with the anode E5 and the current distribution of 3 associated with the anode E6 in FIG. 11 to the remaining anode, namely anode E22. The controller 650 has also redistributed the cathodic current of 6 associated with the cathode E2 and the cathodic current of 4 associated with the cathode E19 in FIG. 11 to the remaining cathode, namely anode E12. In this manner, the complex configuration shown in FIG. 11 can be quickly simplified, e.g., to a bipolar configuration.

Figure 13:
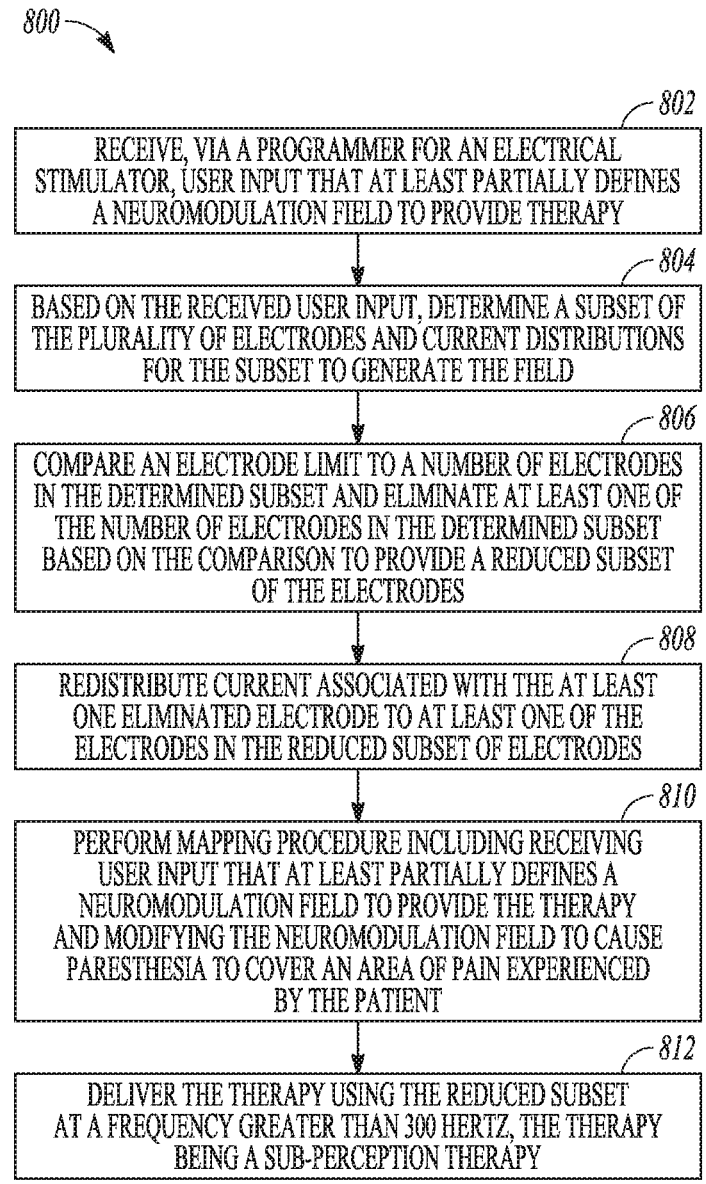
FIG. 13 is a flowchart of an example method of providing therapy to a patient using a plurality of electrodes implanted within the patient in accordance with various techniques of this disclosure.

FIG. 13 is a flowchart of an example method of providing therapy to a patient using a plurality of electrodes implanted within the patient in accordance with various techniques of this disclosure. The example method 800 of FIG. 13 can include receiving, via a programmer for an electrical stimulator, e.g., programming device 602, user input that at least partially defines a neuromodulation field to provide the therapy (block 802). Based on the received user input, a controller, e.g., controller 650 of programming device 650, can determine a subset of the plurality of electrodes and current distributions for the subset to generate the field (804). Using a comparator, e.g., comparator 652, the controller can compare an electrode limit to a number of electrodes in the determined subset and eliminate at least one of the number of electrodes in the determined subset based on the comparison to provide a reduced subset of the electrodes (block 806). The controller can redistribute current associated with the at least one eliminated electrode to at least one of the electrodes in the reduced subset of electrodes (block 808).

The method 800 can optionally include performing a mapping procedure where the mapping procedure includes modifying the neuromodulation field to cause paresthesia to cover an area of pain experienced by the patient (block 810). For example, using the programming device 602, e.g., the GUI 610, the user can modify the neuromodulation field to cause paresthesia to cover an area of pain experienced by the patient, e.g., using the patient's feedback to assist in modifying the field. In some examples, this can include determining the electrodes and current distributions to cover the area of pain.

In some example implementations, once the user has determined that the field has covered the area of pain, the user can provide input to the programming device 602, e.g., using the GUI 610, that modifies the neurostimulation field to not cause the patient to perceive paresthesia. In response, the implantable device, e.g., the electrical stimulator 404 of FIG. 5, can deliver a sub-perception therapy using the reduced subset, e.g., at a frequency greater than 300 Hertz (block 812).

VARIOUS NOTES AND EXAMPLES

Example 1 includes subject matter (such as a method, means for performing acts, machine readable medium including instructions that when performed by a machine cause the machine to performs acts, or an apparatus configured to perform) for providing therapy to a patient using a plurality of electrodes implanted within the patient, comprising: receiving, via a programmer for an electrical stimulator, user input that at least partially defines a neuromodulation field to provide the therapy; based on the received user input, determining a subset of the plurality of electrodes and current distributions for the subset to generate the field; comparing an electrode limit to a number of electrodes in the determined subset and eliminating at least one of the number of electrodes in the determined subset based on the comparison to provide a reduced subset of the electrodes; and redistributing current associated with the at least one eliminated electrode to at least one of the electrodes in the reduced subset of electrodes.

In Example 2, the subject matter of Example 1 can optionally include, wherein the determined subset of the plurality of electrodes includes at least two anodic electrodes and at least two cathodic electrodes to provide the field, and wherein eliminating at least one of the number of electrodes in the determined subset based on the comparison to provide a reduced subset of the electrodes includes at least one of: eliminating one anodic electrode based on the anodic electrode having a lowest associated anodic current distribution for the subset; and eliminating one cathodic electrode based on the cathodic electrode having a lowest associated cathodic current distribution for the subset.

In Example 3, the subject matter of Example 1 can optionally include, wherein the determined subset of the plurality of electrodes includes at least two electrodes having a first polarity to provide the field, and wherein eliminating at least one of the number of electrodes in the determined subset based on the comparison to provide a reduced subset of the electrodes includes: eliminating one of the electrodes having a first polarity based on the electrode having the first polarity having a lowest associated current distribution for the subset; and evenly redistributing a current distribution associated with the eliminated electrode to the remaining electrodes having the first polarity.

In Example 4, the subject matter of Example 1 can optionally include, wherein the determined subset of the plurality of electrodes includes at least two electrodes having a first polarity to provide the field, and wherein eliminating at least one of the number of electrodes in the determined subset based on the comparison to provide a reduced subset of the electrodes includes: eliminating one of the electrodes having a first polarity based on the electrode having the first polarity having a lowest associated current distribution for the subset; and proportionally redistributing a current distribution associated with the eliminated electrode to the remaining electrodes having the first polarity.

In Example 5, the subject matter of one or more of Examples 1-4 can optionally include, wherein eliminating at least one of the number of electrodes in the determined subset based on the comparison to provide a reduced subset of the electrodes comprises: receiving a user selection that allows a user to select the electrode limit.

In Example 6, the subject matter of Example 5 can optionally include, wherein the electrode limit is two electrodes.

In Example 7, the subject matter of one or more of Examples 1-6 can optionally include, wherein the user input that at least partially defines a neurostimulation field causes the patient to perceive paresthesia, the method comprising: receiving user input that modifies the neurostimulation field to not cause the patient to perceive paresthesia.

In Example 8, the subject matter of one or more of Examples 1-7 can optionally include, conveying electrical current to the electrodes remaining in the determined subset of electrodes in accordance with the redistributed current distribution, thereby providing therapy to the patient.

In Example 9, the subject matter of one or more of Examples 1-8 can optionally include, performing a mapping procedure, the mapping procedure including the receiving user input that at least partially defines a neuromodulation field to provide the therapy and modifying the neuromodulation field to cause paresthesia to cover an area of pain experienced by the patient, wherein determining the subset of the plurality of electrodes includes determining the electrodes and current distributions to cover the area of pain, and delivering the therapy using the reduced subset at a frequency greater than 300 Hertz, the therapy being a sub-perception therapy.

In Example 10, the subject matter of one or more of Examples 1-9 can optionally include, displaying, via the programmer, the determined current distributions for the subset; and displaying, via the programmer, redistributed current distributions associated with the reduced subset of electrodes.

Example 11 includes subject matter (such as a device, system, circuit, apparatus, or machine) for providing therapy to a patient using a plurality of electrodes implanted within the patient, comprising: a programmer for an electrical stimulator, the programmer including: a user interface configured to receive user input that at least partially defines a neuromodulation field to provide the therapy; and at least one controller in communication with the user interface, the at least one controller configured to determine a subset of the plurality of electrodes and current distributions for the subset to generate the field based on the received user input; a comparator configured to compare an electrode limit to a number of electrodes in the determined subset and eliminate at least one of the number of electrodes in the determined subset based on the comparison to provide a reduced subset of the electrodes, and the at least one controller configured to redistribute current associated with the at least one eliminated electrode to at least one of the electrodes in the reduced subset of electrodes.

In Example 12, the subject matter of Example 11 can optionally include, wherein the determined subset of the plurality of electrodes includes at least two anodic electrodes and at least two cathodic electrodes to provide the field, and wherein the at least one controller configured to eliminate at least one of the number of electrodes in the determined subset based on the comparison to provide a reduced subset of the electrodes is configured to perform at least one of the following: eliminate one anodic electrode based on the anodic electrode having a lowest associated anodic current distribution for the subset; and eliminate one cathodic electrode based on the cathodic electrode having a lowest associated cathodic current distribution for the subset.

In Example 13, the subject matter of Example 11 can optionally include, wherein the determined subset of the plurality of electrodes includes at least two electrodes having a first polarity to provide the field, and wherein the at least one controller configured to eliminate at least one of the number of electrodes in the determined subset based on the comparison to provide a reduced subset of the electrodes is configured to: eliminate one of the electrodes having a first polarity based on the electrode having the first polarity having a lowest associated current distribution for the subset; and evenly redistribute a current distribution associated with the eliminated electrode to the remaining electrodes having the first polarity.

In Example 14, the subject matter of Example 11 can optionally include, wherein the determined subset of the plurality of electrodes includes at least two electrodes having a first polarity to provide the field, and wherein the at least one controller configured to eliminate at least one of the number of electrodes in the determined subset based on the comparison to provide a reduced subset of the electrodes is configured to: eliminate one of the electrodes having a first polarity based on the electrode having the first polarity having a lowest associated current distribution for the subset; and proportionally redistribute a current distribution associated with the eliminated electrode to the remaining electrodes having the first polarity.

In Example 15, the subject matter of one or more of Examples 11-14 can optionally include, wherein the at least one controller configured to eliminate at least one of the number of electrodes in the determined subset based on the comparison to provide a reduced subset of the electrodes is configured to: receive a user selection that allows a user to select the electrode limit.

In Example 16, the subject matter of Example 15 can optionally include, wherein the electrode limit is two electrodes.

In Example 17, the subject matter of one or more of Examples 11-16 can optionally include, wherein the user input that at least partially defines a neurostimulation field causes the patient to perceive paresthesia, and wherein the user interface is configured to: receive user input that modifies the neurostimulation field to not cause the patient to perceive paresthesia.

In Example 18, the subject matter of one or more of Examples 11-17 can optionally include, the electrical stimulator configured to convey electrical current to the electrodes remaining in the determined subset of electrodes in accordance with the redistributed current distribution, thereby providing therapy to the patient.

In Example 19, the subject matter of one or more of Examples 11-18 can optionally include, wherein the programmer is configured to perform a mapping procedure, the mapping procedure including the user interface being configured to receive user input that at least partially defines a neuromodulation field to provide the therapy and that modifies the neuromodulation field to cause paresthesia to cover an area of pain experienced by the patient, wherein the at least one controller configured to determine the subset of the plurality of electrodes is configured to determine the electrodes and current distributions to cover the area of pain, and wherein the electrical stimulator is configured to deliver the therapy using the reduced subset at a frequency greater than 300 Hertz, the therapy being a sub-perception therapy.

In Example 20, the subject matter of one or more of Examples 11-19 can optionally include, wherein the user interface is configured to: display the determined current distributions for the subset; and display redistributed current distributions associated with the reduced subset of electrodes.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A machine-implemented method of providing therapy to a patient using at least some of a plurality of electrodes implanted within the patient, the method comprising:

receiving, via a programmer for an electrical stimulator, user input that at least partially defines a neuromodulation field to provide the therapy;

based on the received user input, determining a subset of the plurality of electrodes and current distributions for the subset to generate the field;

comparing an electrode limit to a number of electrodes in the determined subset and eliminating at least one of the number of electrodes in the determined subset based on the comparison to provide a reduced subset of the electrodes; and redistributing current associated with the at least one eliminated electrode to at least one of the electrodes in the reduced subset of electrodes.

2. The method of claim 1, wherein the determined subset of the plurality of electrodes includes at least two anodic electrodes and at least two cathodic electrodes to provide the field, and wherein eliminating at least one of the number of electrodes in the determined subset based on the comparison to provide a reduced subset of the electrodes includes at least one of:

eliminating one anodic electrode based on the anodic electrode having a lowest associated anodic current distribution for the subset; and eliminating one cathodic electrode based on the cathodic electrode having a lowest associated cathodic current distribution for the subset.

3. The method of claim 1, wherein the determined subset of the plurality of electrodes includes at least two electrodes having a first polarity to provide the field, and wherein eliminating at least one of the number of electrodes in the determined subset based on the comparison to provide a reduced subset of the electrodes includes:

eliminating one of the electrodes having a first polarity based on the electrode having the first polarity having a lowest associated current distribution for the subset; and evenly redistributing a current distribution associated with the eliminated electrode to the remaining electrodes having the first polarity.

4. The method of claim 1, wherein the determined subset of the plurality of electrodes includes at least two electrodes having a first polarity to provide the field, and wherein eliminating at least one of the number of electrodes in the determined subset based on the comparison to provide a reduced subset of the electrodes includes:

eliminating one of the electrodes having a first polarity based on the electrode having the first polarity having a lowest associated current distribution for the subset; and proportionally redistributing a current distribution associated with the eliminated electrode to the remaining electrodes having the first polarity.

5. The method of claim 1, wherein eliminating at least one of the number of electrodes in the determined subset based on the comparison to provide a reduced subset of the electrodes comprises:

receiving a user selection that allows a user to select the electrode limit.

6. The method of claim 5, wherein the electrode limit is two electrodes.

7. The method of claim 1, wherein the user input that at least partially defines a neurostimulation field causes the patient to perceive paresthesia, the method comprising:

receiving user input that modifies the neurostimulation field to not cause the patient to perceive paresthesia.

8. The method of claim 1, comprising:

conveying electrical current to the electrodes remaining in the determined subset of electrodes in accordance with the redistributed current distribution, thereby providing therapy to the patient.

9. The method of claim 1, further comprising:

performing a mapping procedure, the mapping procedure including the receiving user input that at least partially defines a neuromodulation field to provide the therapy and modifying the neuromodulation field to cause paresthesia to cover an area of pain experienced by the patient, wherein determining the subset of the plurality of electrodes includes determining the electrodes and current distributions to cover the area of pain, and delivering the therapy using the reduced subset at a frequency greater than 300 Hertz, the therapy being a sub-perception therapy.

10. The method of claim 1, comprising:

displaying, via the programmer, the determined current distributions for the subset; and displaying, via the programmer, redistributed current distributions associated with the reduced subset of electrodes.

11. A system of providing therapy to a patient using at least some of a plurality of electrodes implanted within the patient, the system comprising:

a programmer for an electrical stimulator, the programmer including:

a user interface configured to receive user input that at least partially defines a neuromodulation field to provide the therapy; and at least one controller in communication with the user interface, the at least one controller configured to determine a subset of the plurality of electrodes and current distributions for the subset to generate the field based on the received user input;

a comparator configured to compare an electrode limit to a number of electrodes in the determined subset and eliminate at least one of the number of electrodes in the determined subset based on the comparison to provide a reduced subset of the electrodes, and the at least one controller configured to redistribute current associated with the at least one eliminated electrode to at least one of the electrodes in the reduced subset of electrodes.

12. The system of claim 11, wherein the determined subset of the plurality of electrodes includes at least two anodic electrodes and at least two cathodic electrodes to provide the field, and wherein the at least one controller configured to eliminate at least one of the number of electrodes in the determined subset based on the comparison to provide a reduced subset of the electrodes is configured to perform at least one of the following:

eliminate one anodic electrode based on the anodic electrode having a lowest associated anodic current distribution for the subset; and eliminate one cathodic electrode based on the cathodic electrode having a lowest associated cathodic current distribution for the subset.

13. The system of claim 11, wherein the determined subset of the plurality of electrodes includes at least two electrodes having a first polarity to provide the field, and wherein the at least one controller configured to eliminate at least one of the number of electrodes in the determined subset based on the comparison to provide a reduced subset of the electrodes is configured to:

eliminate one of the electrodes having a first polarity based on the electrode having the first polarity having a lowest associated current distribution for the subset; and evenly redistribute a current distribution associated with the eliminated electrode to the remaining electrodes having the first polarity.

14. The system of claim 11, wherein the determined subset of the plurality of electrodes includes at least two electrodes having a first polarity to provide the field, and wherein the at least one controller configured to eliminate at least one of the number of electrodes in the determined subset based on the comparison to provide a reduced subset of the electrodes is configured to:

eliminate one of the electrodes having a first polarity based on the electrode having the first polarity having a lowest associated current distribution for the subset; and proportionally redistribute a current distribution associated with the eliminated electrode to the remaining electrodes having the first polarity.

15. The system of claim 11, wherein the at least one controller configured to eliminate at least one of the number of electrodes in the determined subset based on the comparison to provide a reduced subset of the electrodes is configured to:

receive a user selection that allows a user to select the electrode limit.

16. The system of claim 15, wherein the electrode limit is two electrodes.

17. The system of claim 11, wherein the user input that at least partially defines a neurostimulation field causes the patient to perceive paresthesia, and wherein the user interface is configured to:

receive user input that modifies the neurostimulation field to not cause the patient to perceive paresthesia.

18. The system of claim 11, comprising:

the electrical stimulator configured to convey electrical current to the electrodes remaining in the determined subset of electrodes in accordance with the redistributed current distribution, thereby providing therapy to the patient.

19. The system of claim 1, wherein the programmer is configured to perform a mapping procedure, the mapping procedure including the user interface being configured to receive user input that at least partially defines a neuromodulation field to provide the therapy and that modifies the neuromodulation field to cause paresthesia to cover an area of pain experienced by the patient, wherein the at least one controller configured to determine the subset of the plurality of electrodes is configured to determine the electrodes and current distributions to cover the area of pain, and wherein the electrical stimulator is configured to deliver the therapy using the reduced subset at a frequency greater than 300 Hertz, the therapy being a sub-perception therapy.

20. The system of claim 11, wherein the user interface is configured to:

display the determined current distributions for the subset; and display redistributed current distributions associated with the reduced subset of electrodes.

\* \* \* \* \*